United States Patent [19]
Katti et al.

[11] Patent Number: 5,948,386
[45] Date of Patent: Sep. 7, 1999

[54] CONJUGATE AND METHOD FOR FORMING AMINOMETHYL PHOSPHORUS CONJUGATES

[75] Inventors: Kattesh V. Katti; Douglas E. Berning; Wynn A. Volkert; Alan R. Ketring; Robert Churchill, all of Columbia, Mo.

[73] Assignee: The Curators of the University of Missouri, Columbia, Mo.

[21] Appl. No.: 08/818,075

[22] Filed: Mar. 14, 1997

[51] Int. Cl.$^6$ ............................ A61K 51/00; A61M 36/14
[52] U.S. Cl. ...................... 424/1.77; 424/1.77; 424/1.11; 424/1.45; 424/1.49; 424/1.69; 568/8
[58] Field of Search .................................. 424/1.11, 1.37, 424/1.61, 1.77, 9.1, 9.3, 9.4, 9.5, 1.65, 1.69, 1.49, 1.45; 568/8, 10; 562/8; 564/12, 15; 534/7, 10–16

[56] References Cited

U.S. PATENT DOCUMENTS 5,855,867  1/1999  Katti et al. ............................. 424/1.77

OTHER PUBLICATIONS

Angolini, (Tramontini and Angiolini) (1990) Further advances in the chemistry of mannich bases. *Tetrahedron*, 46:1791–1837.

Annuziato et al., (1993) p–Maleimidophenyl Isocyanate: a novel heterobifunctional linker for hydroxyl to thiol coupling. *Bioconjugate Chem.*, 54, pp. 212, 218.

Brewster et al., (1989) The potential uses of cyclodextrins in parenteral formulations. *J. Parenteral Sci. Technol.*, 43:231–240.

Cox et al. (1990) Synthesis of C–and N–functionalised derivatives of 1,4,7–triazacyclonon–ane–1,4,7–triyltriacetic acid . . . *J. Chem. Soc. Perkin Trans.*, 1:2567–2576.

Duchene et al., (1987) Pharmaceutical applications of cyclodextrins. in *Cyclodextrins and their industrial uses*, editions de Sante Paris, pp. 211–257.

Eisch and Sanchez (1986) Selective, oxophilic imination of ketones with Bis(dichloroaluminum) phenylimide. *J. Org. Chem.*, 51:1848–1852.

Frank and Drake, (1972) Aniline derivatives of tetrakis(hydroxy–methyl)phosphonium chloride. *J. Org. Chem.*, 37:2752–2755.

Hayashi and Ikada (1991) Protease immobilization onto porous chitosan beads. *J. Appl. Polym. Sci.*, 42:85–92.

Kline et al., (1991) Carboxymethyl–substituted bifunctional chelators: preparation of aryl isothiocyanate derivatives . . . *Bioconjugate Chemistry*, 2:26–31.

Krajwska et al., (1990) Urease immobilized on chitosan membrane: preparation and properties *J. Chem. Tech. Biotechnol.*, 48:337–50.

Lewis et al., (1994) A facile, water–soluble method for modification of proteins with DOTA. Use of elevated temperature . . . *Bioconjugate Chemistry*, 5:565–576.

Liu et al., (1996) Labeling a hydrazino nicotinamide–modified cyclic IIb/IIIa receptor antagonist . . . *Bioconjugate Chemistry*, 7:63–71.

Moi et al. (1988) The peptide way to macrocyclic bifunctional chelating agents: synthesis of 2–(p–Nitrobenzyl)–1, 4,7,10 . . . *J. MA. Chem. Soc.*, 110:6266–6267.

Petach et al., (1994) $P(CH_2OH)_3$–A new coupling reagent for the covalent immobilisation of enzymes. *J. Chem. Soc. Chem. Commun.*, p. 2181.

Reeves and Guthrie, (1956) Intermedicate for flame–resistant polymers: reactions of Tetrakis(hydroxymethyl)phosphonium chloride. *Ind. Eng. Chem.*, 48:67–67.

Schubiger et al. (1996) Vehicles, chelators, and radionuclides: choosing the "building blocks" of an effective therapeutic . . . *Bioconjugate Chemistry*, 7:165–179.

*Primary Examiner*—Jose'G. Dees
*Assistant Examiner*—Dameron Jones
*Attorney, Agent, or Firm*—Kohn & Associates

[57] ABSTRACT

A method of forming phosphine-amine conjugates includes reacting a hydroxymethyl phosphine group of an amine-free first molecule with at least one free amine group of a second molecule to covalently bond the first molecule with the second molecule through an aminomethyl phosphorus linkage and the conjugates formed thereby.

36 Claims, 9 Drawing Sheets

$^{31}P, ^{1}H, ^{13}C$ NMR
Hetcor, COSY
HR FABMS $R = CH_2 OH = N$-acetylserine $R = CH_2 SH = N\alpha$-acetylcysteine $R = CH_2 CONH_2 = N\alpha$-acetyl-asparagine $R = CH_2 CH_2 CH_2 NHC(NH_2)_2^+ = N\alpha$-acetyl-arginine

Fig-16

CONJUGATE AND METHOD FOR FORMING AMINOMETHYL PHOSPHORUS CONJUGATES

GRANT REFERENCE

The research carried out in connection with this invention was supported in part by a grant from the Department of Energy (DOE) DOE-DE-FG0289ER60875. The Government has certain rights in the invention.

TECHNICAL FIELD

The present invention relates to employing the reaction of hydroxymethylphosphine (HMP) with primary or secondary amines over a wide pH range to form well-defined conjugate products. More specifically, the present invention relates to methods of using a compound containing an HMP group appended at a specific position on the molecule to covalently couple with a free amine group on another molecule to form an aminomethyl phosphorus linkage.

BACKGROUND OF THE INVENTION

Conjugation of molecular entities to other molecules or materials is used in formulation of a wide variety of compounds or materials used for medicine, biology, industrial processes, etc. (Hayashi and Ikada, 1991, Petach et al., 1994, and Krajwska et al., 1990). For many applications, particularly in the biomedical areas, formation of well-defined covalent linkages between two compounds or substances must be performed in aqueous solutions (Brewster et al., 1989, Schubiger et al., 1996, Duchene et al., 1987).

Many reaction pathways are being used to form specific covalent bonds between compounds (Duchene et al., 1987, Annuziato et al., 1993, and Liu et al., 1996). One of the most common approaches is to react an active functional group with amine groups in a highly specific manner (Schubiger et al., 1996, Lewis et al., 1994). For example, conjugation of monoclonal antibodies or other proteins in aqueous solution with a spectrum of molecular species including, for example, drugs, toxins, fluorescent molecules, and metal chelates, is frequently effected through the formation of a covalent bond. For example, the bond can be amide or imidate bonds, with amine group(s) on the biomolecule (Duchene et al., 1987, Annuziato et al., 1993, Liu et al., 1996, Lewis et al., 1994, Moi et al., 1988, Cox et al., 1990, Kline et al., 1991).

The use of HMP group(s) to conjugate or cross-link one molecule to another molecule or substance containing one or more amine groups provides a novel alternative to other methods currently in use to produce well-defined conjugates. It is known that —$CH_2OH$ sidearms on tris (hydroxymethyl) phosphine (THP) react with amines by Mannich-type condensation reactions with amine groups in aqueous solutions giving aminomethylphosphines (Angiolini, 1990). THP, the most simple HMP ligand, has recently been used to immobilize enzymes (Hayashi and Ikada, 1991, Petach et al., 1994). In that study, THP was mixed with a resin, in bulk, for one hour. The resin was washed in a solution containing urease enzyme and, after incubation for six hours, the immobilized urease was rinsed several times with buffer (Petach et al., 1994). While this application with THP demonstrated the feasibility of using this simple ligand as an immobilization agent, the immobilized products produced were not defined and, undoubtedly, contained a mixture of products including polymers and other compounds possessing undefined aminomethylphosphines linkages. In addition, the effect of pH on both reaction yields and/or product distribution of this method is unknown. Because that study was performed in bulk using non-stoichiometric quantities of reagents, the immobilization yields appear to be low, particularly since no estimates of reaction yields were provided (Petach et al., 1994).

In order for HMP groups to be used as effective functionalities for conjugation or cross-linking one molecule to another compound or substance, their reactions with amines must 1) result in formation of well-defined covalent linkages and 2) form that linkage in high yields. Furthermore, it would also be desirable that the conjugation or cross-linking reactions be conducted under relatively mild conditions over a wide pH range in aqueous solutions, particularly for those involving biomolecules.

Even though THP is known to react with amines via a Mannich-type condensation, the studies to determine the yields, rates of reactions, and conditions required to produce a specific type bonding between HMP groups and amines have, to date, not been performed. For example, it is assumed that the only bond formed when hydroxymethylphosphines react with primary amines is P—$CH_2$—N (H)—linkage (Petach et al., 1994). In addition, the HMP containing molecule THP is expected to react with amine groups to produce polymeric products (Reaves and Guthrie, 1956).

In contrast, applicants have demonstrated, as set forth below, that HMP-containing compounds containing two HMP groups separated by two carbon atoms can react with primary amines in aqueous solutions to form a cyclical linkage (i.e., —PN—). Further, applicants have found that HMP groups react efficiently with amines over a wide pH range (i.e., pH 2–9) and that a specific linkage can be formed in high yields. Applicants have also demonstrated that HMP groups can react with secondary amine groups under similar conditions where the linear P—$CH_2$—N(R) linkage (where R≠H) is formed and in high yields.

The results of the studies reported herein demonstrate that HMP groups, under appropriate reaction conditions, can form a specific aminomethyl-phosphorus bond in high yields with amine groups in aqueous solutions. These results provide evidence that HMP reaction(s) with amines can be used as a vehicle for conjugation or cross-linking one compound with another compound or substance in aqueous media over a wide pH range (i.e., pH 2–9). The resulting conjugated or cross-linked product will be a well-defined chemical entity.

Until recently, very few compounds of this type have been synthesized (Hayashi and Ikada, 1991, Petach et al., 1994, Frank and Drake, 1972). A major reason for paucity of $RP(CH_2OH)_2$ compounds relates to the difficulties in their synthesis. Since these types of compounds have not been available, characterization of HMP group reactions with amines has not been fully elucidated. Recent efforts by applicants to develop strategies for the synthesis of a variety of HMP-based compounds have been successful. With the availability of new HMP-containing compounds, applicants have been able to study the HMP-amine reactions in aqueous solutions under various conditions, including variations in pH. Furthermore, the new synthetic methods developed by applicants have provided evidence that it is possible to synthesize and chemically characterize a wide variety of compounds containing one or more HMP functionalities attached at a predetermined position on the molecule. These fully characterized molecules can, be used to conjugate or cross-link one molecule containing a HMP group to another molecule or material possessing primary or secondary amine group(s) located at specific site or sites on the molecule.

Therefore, it would be both desirable and advantageous to have a method for conjugating or cross-linking one molecule to another compound or substance which results in the formation of well-defined covalent linkages in high yields. Furthermore, it would also be desirable that the conjugation and/or cross-linking reactions be conducted under relatively mild conditions over a wide pH range in aqueous solutions, particularly for those involving biomolecules.

SUMMARY OF THE INVENTION AND ADVANTAGES

In accordance with the present invention, there is provided a method of forming phosphine-amine conjugates which includes reacting a hydroxymethyl phosphine group of an amine-free first molecule with at least one free amine group of a second molecule to covalently bond the first molecule with the second molecule through an aminomethyl phosphorus linkage.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Generally, the present invention provides a method of forming phosphine-amine conjugates which includes reacting a hydroxymethyl phosphine (HMP) group of an amine-free first molecule with at least one free amine group of a second molecule to covalently bond the first molecule with the second molecule through an aminomethyl phosphorus linkage.

The present invention employs the reaction of HMP group(s) (R—P(CH$_2$OH)$_2$, where R can, for example include —CH$_2$OH, H, C$_2$H$_5$, C$_6$H$_5$, —COOH, COOCH$_3$, and COOC$_2$H$_5$, with primary and/or secondary amines over a wide pH range to form well-defined conjugate products in which a specific molecule is covalently linked to a different molecule or solid surface. More specifically, the present invention teaches methods of using compounds containing an a HMP group appended at a specific position on the molecule to covalently couple with a free amine group on an other molecule (or solid surface) to form a well-defined aminomethyl phosphorus linkage as generally shown in the Figures.

Applicants have demonstrated that molecules such as —R—NH2, where R can be a peptide or protein, e.g., collagen, steroids, etc., containing two HMP groups separated by two carbon atoms can react with primary amines in aqueous solutions to form a cyclical linkage (i.e.,—PN—) as exemplified in FIGS. 10–13, and 15. Additionally, applicants have found that HMP groups react efficiently with amines over a wide pH range (i.e., pH 2–9) and that a specific linkage can thus be formed in high yields. Applicants have also demonstrated that HMP groups can react with secondary amine groups under similar conditions where a linear P)- CH$_2$—N(R) linkage (where R≠H) is formed in high yields as exemplified in FIGS. 1–9 where —R can be a peptide or protein, e.g., collagen, steroids, etc.

The results, as set forth in the examples below, support applicants assertion that HMP groups, under appropriate reaction conditions, can form a specific aminomethylphosphorus bond in high yields with amine groups in aqueous solutions. As a result of this reaction, HMP reaction (s) with amines can be used as a vehicle for conjugation or cross-linking one compound with another compound or substance in aqueous media over a wide pH range. The resulting conjugated or cross-linked product being a well-defined chemical entity.

To fully exploit this advance in technology, it is essential that the compounds or cross-linking reagents containing appended HMP group(s) be synthesized ($RP(CH_2OH)_2$, where $R \neq CH_2OH$ and is any other organic molecule or group, such as —$CH_2OH$, H, $C_2H_5$, $C_6H_5$, —COOH, $COOCH_3$, and $COOC_2H_5$, that can be specifically conjugated to another molecule via the reaction of the HMP group with a primary or secondary amine) on the material or compound to be conjugated With the availability of new HMP-containing compounds, applicants have studied the HMP-amine reactions in aqueous solutions under various conditions (e.g., pH). Utilizing these new compounds, new synthetic methods have been developed which make it possible to synthesize and chemically characterize a wide variety of compounds containing one (or more) HMP functionalities attached at a predetermined position on a molecule.

In a preferred embodiment, the HMP groups are separated by two carbon atoms. These fully characterized molecules can, in turn, be used to conjugate or cross-link one molecule containing an HMP group to another molecule or material that has a primary and/or secondary amine group (s) located at a specific site or sites on the molecule.

Figure 1:
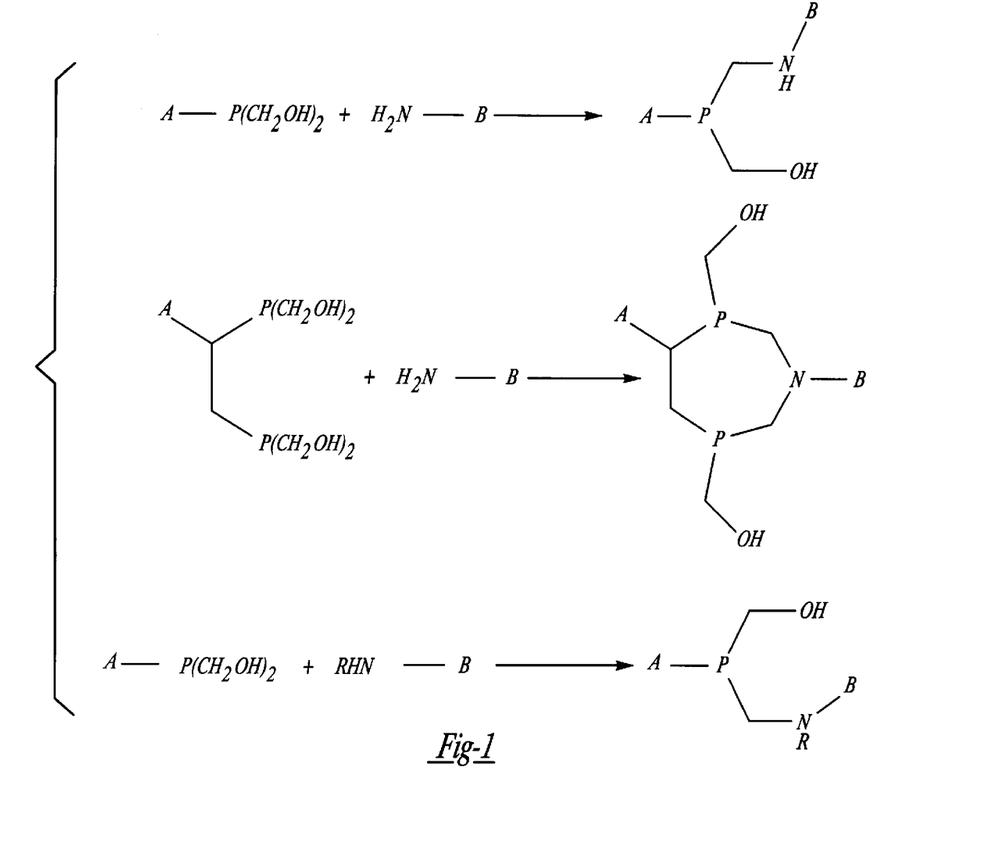
FIG. 1 illustrates the conjugation or cross-linking of a molecule containing a HMP group to another molecule that has an amine group on the molecule wherein A is a molecule or substance containing a HMP group and B is a molecule containing an amine group wherein R≠W H or CH$_2$OH.

The general reaction scheme set forth above for the reaction of HMP-containing compounds with an amine group is shown in FIG. 1 wherein A represents a molecule or substance containing an HMP group to be conjugated to a molecule or substance B containing an amine group via one of the two amino methyl phosphorus linkages where $R \neq H$ or $CH_2OH$.

The conjugation or cross-linker technology of the present invention has broad applicability and can be used to covalently link a wide spectrum of compounds containing one (or two) HMP group(s) to other compounds or substances containing a primary or secondary amine group.

Several reactive groups are being used to covalently link molecules to other molecules or materials via their reaction with amine groups (Duchene et al., 1987, Annuziato et al., 1993, Liu et al., 1996, Lewis et al., 1994, Moi et al., 1988, Cox et al., 1990, Kline et al., 1991). While many reactions can be carried out using non-polar solvents, many must be conducted in aqueous solutions, particularly those conjugation or cross-linking of biomolecules (Schubiger et al., 1996. Duchene et al., 1987, Annuziato et al., 1993, Liu et al., 1996, Lewis et al., 1994, Moi et al., 1988, Cox et al., 1990, Kline et al., 1991). In most cases, the reactive groups (incl., activated esters, anhydrides, imidates, arylthiocyanates, etc.) require that the pH of the aqueous media is >7 (often in the range of 8.5–9.5 or greater) to maximize the fraction of the targeted amine groups that are in the unprotonated form in order to provide a reasonably efficient conjugation reaction (Schubiger et al., 1996, Duchene et al., 1987, Annuziato et al., 1993, Liu et al., 1996, Lewis et al., 1994, Moi et al., 1988, Cox et al., 1990 Kline et al., 1991). Other cross-linking agents that have been used at lower pH's (i.e., pH<8) either produce low yields or unstable products.

For example, glutaraldehyde and other aldehydes react with primary amines to produce imines (i.e., C=N—) (Eisch and Sanchez, 1986). These linkages have limited stability and must often be reduced to the respective amines to provide acceptable stability. Reduction of imine bonds requires harsh conditions that cannot be used with proteins and many other biomolecules. In addition, most of these reagents can efficiently react with only primary amines (and not secondary amines). Hydrolysis of most of the other reactive groups that target amines at basic pH is also a problem as the rate of their hydrolysis competes with the rate of their reaction with primary amines (Lewis et al., 1994). This limits the yield of the desired amine-coupled product (Lewis et al., 1994). A functional group that is not hydrolyzed in aqueous solutions and is capable of reacting with amines at lower pH$\leq$7–8 to form a well-defined and stable covalent linkage(s) with amine groups in high yields would offer a major improvement over existing technology for many applications (see examples below).

Figure 2:
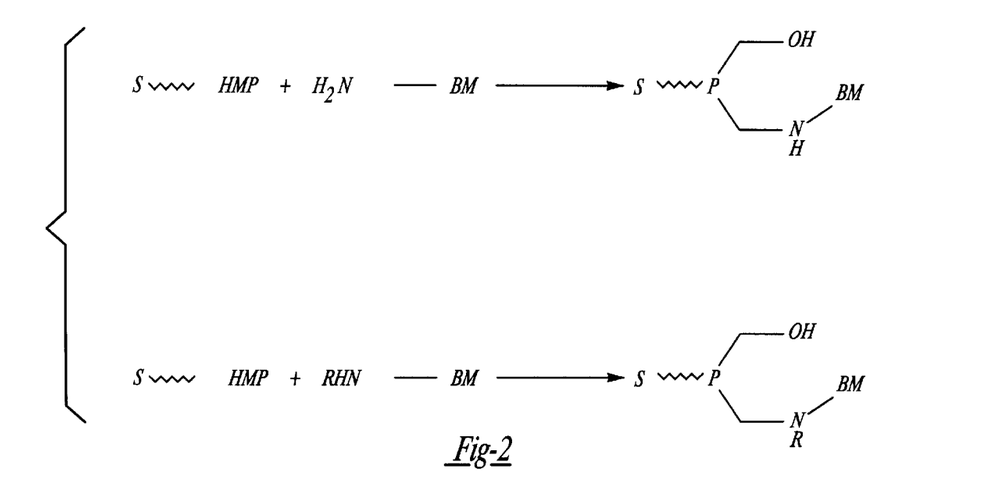
FIG. 2 illustrates the conjugation or cross-linking of HMP-derivatives with biomolecules (BM)

This conjugation technology has extremely broad applicability. HMP-derivatives of virtually any molecule (that does not contain amine groups) can be conjugated to other materials that contain one or more amine groups. This includes linking drugs, fluorescent probes, toxins, radioactive moieties, etc., to biomolecules (BMs) (e.g., monoclonal antibodies and other molecules that have high affininity toward breast tumor receptors such as progesterone, estradiol, and progestin) in high yields over a wide pH range, as shown in FIG. 2, where (S) is any molecular species (not containing an amine functionality and $R \neq H$).

Figure 3:
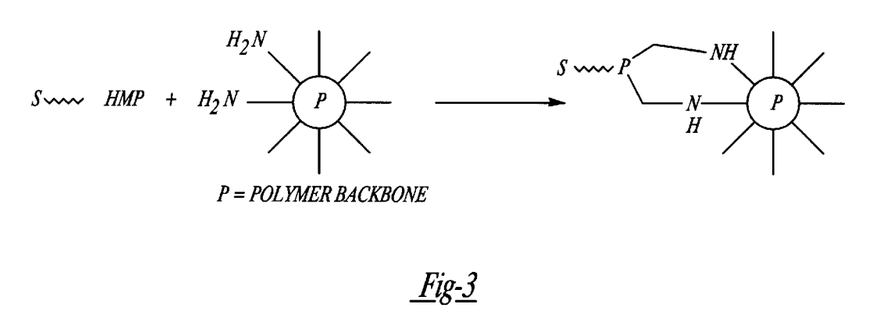
FIG. 3 illustrates the linkage of molecules to non-biologically active molecules or solid surfaces wherein S represents a molecule linked to a solid support (P=polymer backbone)

Additionally, the reactions of the present invention can be utilized to link a spectrum of molecules to other non-biologically active molecules or solid surfaces such as separation columns, solid matrices, or other solid surfaces known to those skilled in the art. Referring to FIG. 3, molecules (S) are linked to solid surfaces containing primary or secondary amine groups to rapidly and efficiently link the molecules (S) to the solid surface.

Figure 4:
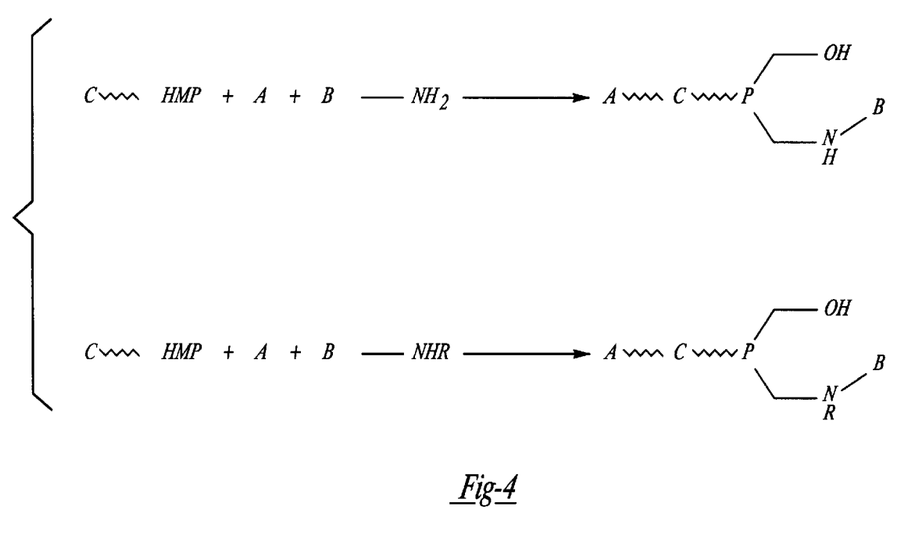
FIG. 4 illustrates the use of HMP groups as one of two reactive groups in hetero- or homo-bifunctional cross-linking reagents to construct a bifunctional cross-linking agent containing one HMP group attached via a spacer group to another chemically active group wherein A is a molecule containing a site that will specifically react with chemically reactive group C (other than with HMP group) on the cross linker.

Referring to FIG. 4, HMP groups can also be used as one of two reactive groups of hetero-or homo-bifunctional cross-linking reagents which are similar in design to those previously and currently using other chemically reactive functionalities. For example, a bifunctional cross-linking agent containing one HMP group attached via a spacer group to another chemically active group (either another HMP group or a different group) can be prepared where (A) is a molecule containing a site that will specifically react with chemically reactive group (C) (other than with the HMP group) on the cross-linker (C~HMP). The HMP group reacts with the amine group (s) on molecule (B) where $R \neq H$.

Figure 5:
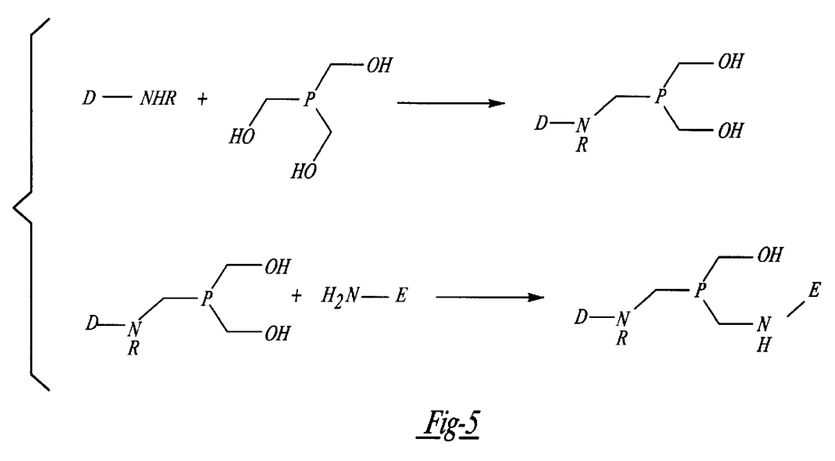
FIG. 5 illustrates the use of tris-hydroxymethyl phosphine (THP) to cross-link two different molecules in aqueous or alcoholic solutions, wherein THP is reacted with a molecule D with a secondary amine group and is then reacted with a second molecule E containing a primary amine group.
Figure 6:
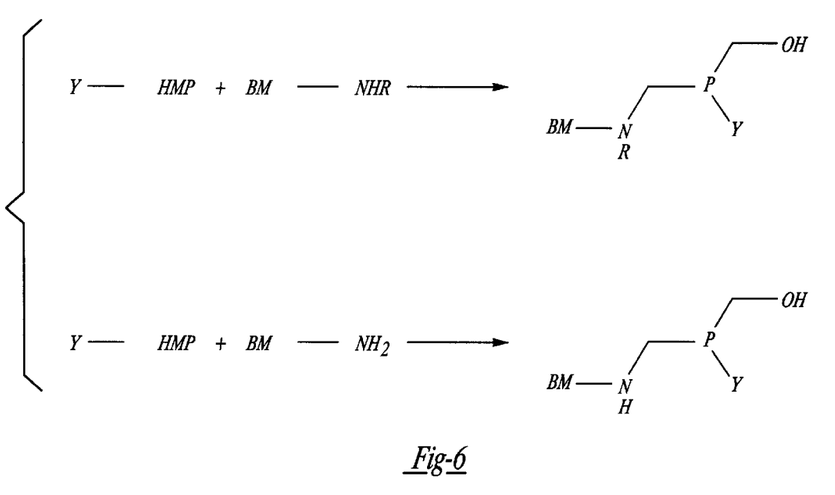
FIG. 6 illustrates a general method of conjugating "preformed" radiolabeled moieties, chelating agents, and a variety of non-radioactive molecules to a bioactive molecule, wherein BM is the bioactive molecule containing an amine group [—NH(R)] where R=H or other side chain and Y is a chelating agent used to specifically bind radionuclidies, a "pre-formed" radiolabeled moiety, or any non-radioactive molecule to which is appended a HMP functionality.

Referring to FIG. 5, tris-hydroxymethyl phosphine (THP) is utilized to conveniently cross-link two different molecules or moieties in aqueous or alcoholic solutions. This reaction involves a slight excess of THP with one molecule (D) with a secondary amine group, separation of the excess THP, and then reacting a second molecule (E) containing a primary amine group with the THP-derivatized molecule (D) where R is a side chain (a small alkyl group) other than H.

The present invention also provides a general method for conjugating "pre-formed" radiolabeled moieties, chelating agents, and a variety of non-radioactive molecules to bioactive molecules. This general method is set forth in FIG. 6 wherein (BM) represents a bioactive molecule containing an amine group [—NH(R)], where R=H or other side chain (e.g., small chain alkyl group) and (Y) represents a chelating agent (to be used to specifically bind radionuclides), a "pre-formed" radiolabeled moiety, or any non-radioactive molecule, including fluorescent molecules, drugs, toxins, etc., to which is appended via a side arm, a HMP functionality. The (Y) group will be covalently linked to the (BM) by formation of the aminomethyl phosphorus bond. This reaction provides a novel method for linking a wide variety of chemical moieties to bioactive molecules at mild and acidic pH (pH<8).

Figure 7:
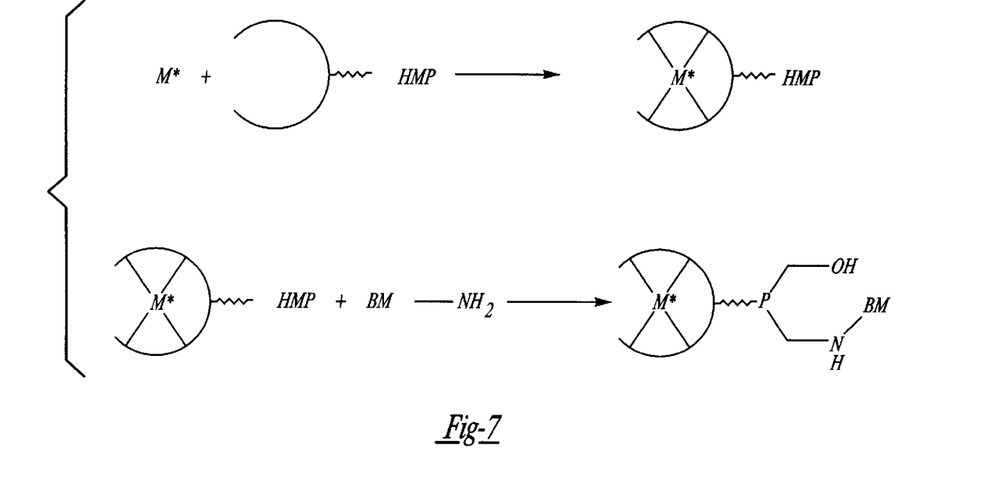
FIG. 7 illustrates a reaction sequence leading to the formation of a radiopharmaceutical wherein )- is a chelating agent covalently linked to a HMP group to form )-HMP bifunctional chelating agent (BFCA) that will form a stable complex with a metallic radionuclide M.

For radiopharmaceutical applications, the "pre-formed" radiolabeled moieties can include a spectrum of chelates that have already been complexed to radionuclides which can be used to produce diagnostic and/or therapeutic radiopharmaceuticals (Moi et al., 1988). The reaction sequence for the preparation of a radiopharmaceutical according to this method is shown in FIG. 7. In FIG. 7, )- is a chelating agent covalently linked to a HMP group to form a )^^ HMP bifunctional chelating agent or BFCA (Cox et al., 1990) that will form a stable complex in high yields with a diagnostically or therapeutically useful metallic radionuclide (i.e., M*) (incl., $^{99m}Tc$, $^{186}Re$, $^{188}Re$, $^{111}In$, $^{90}Y$, $^{199}Au$, $^{105}Rh$, $^{64/67}Cu$, $^{153}Sm$, $^{166}Ho$, $^{177}La$, and others considered to hold potential for radiopharmaceutical applications) (Kline et al., 1991). In addition, HMP-side arms can be attached to several different chelating agents that have been previously reported (e.g., DTPA, DOTA, diamidiodithiol, triamidiomonothiol and other ligand frameworks) (Angiolini, 1990) to have potential usefulness in radiopharmaceutical design. In contrast, linking these chelating agents or "performed" radiolabeled chelates by conjugating amine containing molecules with the different reactive groups previously reported (e.g., NHS, activated esters, etc.) at pH>8 (Frank and Drake 1972), the HMP based BFCAs or bifunctional chelates of the present invention can be conjugated via reaction of the appended HMP group with an amine group on the (BM) at pH$\leq$8 during the formulation process for radiopharmaceuticals.

The utility of using HMP groups to covalently link moieties with a variety of molecules (e.g., peptides) is enhanced by the high selectivity of their reaction with primary and secondary amine groups. The HMP groups have either no or low reactivity with any of the functionalities found on proteins or peptides other than amines. Specifically, as set forth below, applicants have demonstrated that HMP groups have low or no reactivity, in aqueous solutions, with the following groups: primary or secondary amido, thiol and thioether, alcohol, guanidino, imidazole, and indole groups (see FIG. 16). In contrast, HMP groups react efficiently with primary and secondary amines under the same conditions as studied with these other functional groups that are present on peptides or proteins. The results outlined herein demonstrate the high selectivity that HMP groups have in reacting with amines on proteins and peptides.

Long-term storage of HMP containing compounds can be facilitated by converting HMP-groups to the respective phosphorus oxides and sulfides. These phosphorus oxides or sulfide groups (e.g., R—P(E)(CH$_2$OH)$_2$, where E=O or S) can rapidly and selectively be converted quantitatively to the respective HMP-phosphine group(s) using mild conditions using silicon based reducing agents. Thus, the HMP containing conjugating or cross-linking agents can be rapidly generated by reduction of the respective phosphorous oxide or sulfide groups using the silicon based reducing agents and are ready for use in conjugating moieties or cross-linking compounds via the amine groups. Applicants have shown that these silicon based reducing agents will rapidly reduce RP(E)(CH$_2$OH)$_2$ to RP(CH$_2$OH)$_2$ while not causing reduction or modification of other functionalities on peptides.

Figure 8:
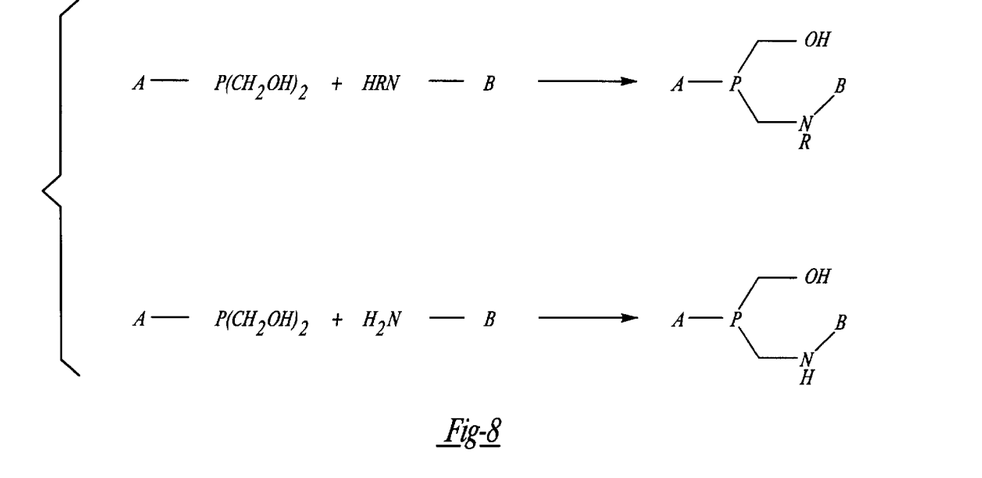
FIG. 8 illustrates the conjugation or cross-linking of a molecule containing a HMP group to another molecule having a primary or secondary amine group S on the molecule wherein A is a molecule containing a HMP group that will be conjugated to a molecule or substance B containing an amine group via one of two aminomethylphosphorus linkages.

FIG. 8 illustrates the reaction scheme wherein "conjugating agents," when mixed with other molecules containing either a primary or secondary amine or group (e.g., bioactive molecules or substances containing an amine group(s), will react via the appended HMP group in highspecificity, with the free amine group(s) to form covalent linkages by simply mixing the reactions in aqueous media over a wide pH range.

EXAMPLES

This experimental section illustrates the formation of well-defined (non-cross-linked) phosphine-amine conjugates. These examples include reactions of P(CH$_2$OH)$_3$; THP (CH$_2$OH)$_2$PRP(CH$_2$OH)$_2$ (R=O—C$_6$H$_4$; HMPB; —CH$_2$—CH$_2$; HMPE) and PhP(CHOH)$_2$ with both primary amines and secondary amines, the synthesis of an N$_2$P$_2$ cheating system, and the reduction of a pentavalent phosphine oxide to the corresponding phosphines. In addition, results of studies showing that HMP groups do not react with other functional or proteins, other than amine groups are provided.

General:

All reactions were carried out under purified nitrogen by standard Schlenk techniques as is well known in the art. Solvents were purified and dried by standard methods and distilled under nitrogen prior to use. Glycine, alanine and gly-gly-gly were obtained from Sigma Chemical Co. Diethylamine and N-methylaniline were obtained from Aldrich Chemical Co. All commercially available reagents were used without further purification. THP was prepared as previously described (Hayashi and Ikada, 1991, Petach et al., 1994). Nuclear magnetic resonance spectra were recorded on a Bruker ARX-300 spectrometer. The $^1$H and $^{13}$C chemical shifts are reported relative to an external standard of TMS, while $^{31}$P NMR chemical shifts to 85% H$_3$PO$_4$. High pressure liquid chromatography (HPLC) analyses and separations were performed using a Waters 600 dual pump system equipped with a 486 tunable absorbance detector and a 746 data module. Standard reverse phase HPLC separations were preformed on a C18 column (Whatman Partisil 10 ODS-3 (9.5×500 mm)) using a gradient mobile phase with solvent A composed of 0.1% trifluoroacetic acid in a 3:1 acetonitrile: water mixture and solvent B composed of 0.1% trifluoroacetic acid in water. The gradient used was as follows: 0–3 min 2% A, 98% B; 3–18 minute linear gradient to 100% A; 18–20 minute 100% A; 20–30 minute linear gradient to 2% A, 98% B. The flow rate and wavelengths were set to 4 ml/min and 254 nm; respectively. Mass-spectral analyses were performed by the Washington University Resource for Biomedical and Bioorganic Mass Spectrometry, St. Louis, Mo. Elemental Analyses were performed by Oneida Research Services, Inc. Whitesboro, N.Y. Melting points were determined on Mel-Temp II apparatus and are uncorrected. All the reactions summarized below occurred in the pH range 2–9.

Figure 9:
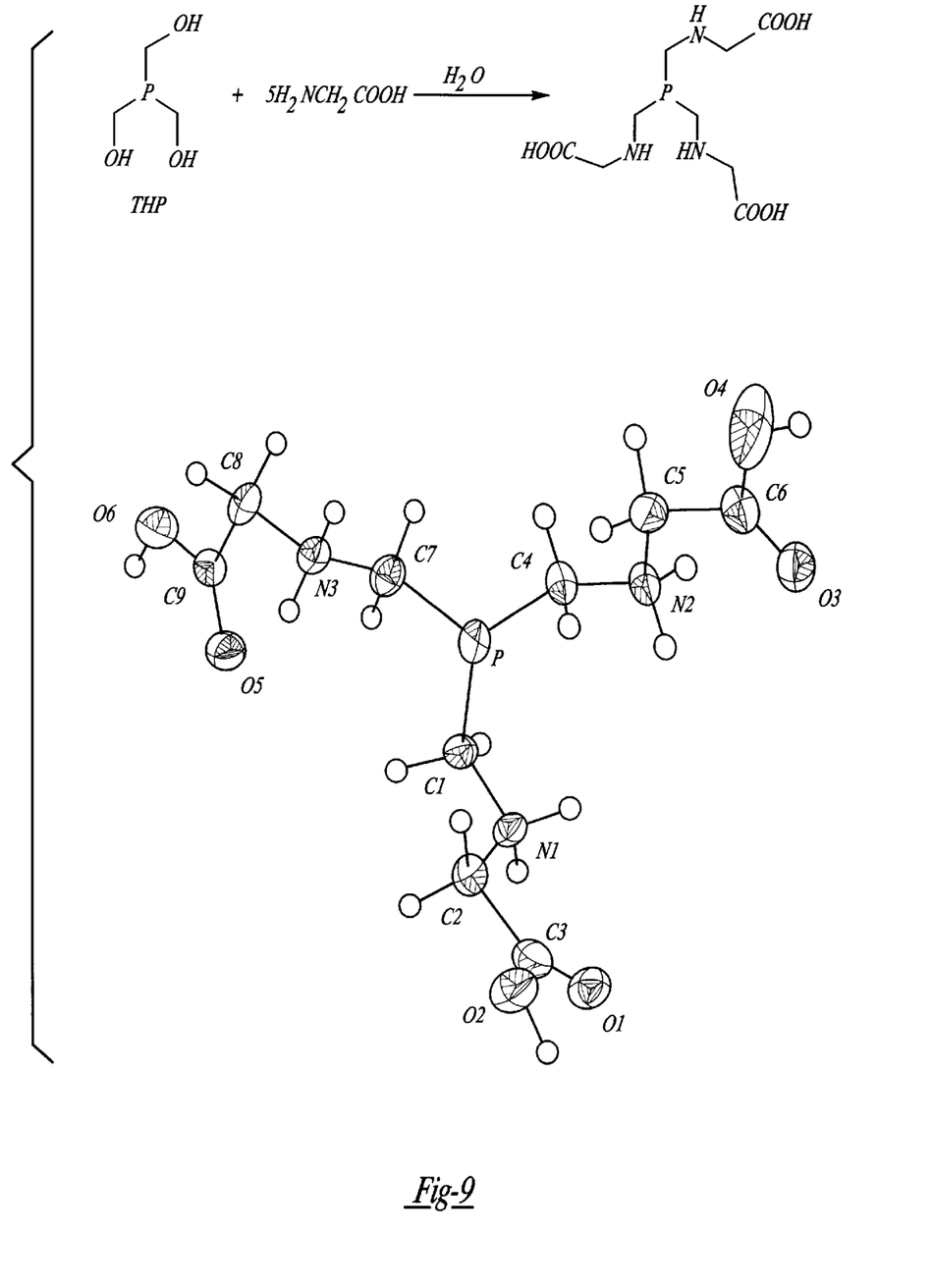
FIG. 9 illustrates the reaction of HMPB with glycine.

Reaction of P(CH$_2$OH)$_3$ with Glycine (FIG. 9)

TMP (7.52 mmol.) in 10 mL of distilled water was added dropwise to glycine (3.76 mmol.) in water (10 mL) at 25° C. The reaction was stirred under dry nitrogen for three hours. The product was filtered off and dried in vacuo to give the analytically pure compounds in 80% yield as a white solid. Crystals suitable for x-ray analysis were obtained from methanol/hydrochloric acid at −20° C. Anal. Calcd. for C$_9$H$_{18}$N$_3$O$_6$P: C, 36.61; H, 6.14: N, 14.24. Found: C, 32.75; H, 6.34; N, 13.14. HRFAB Calcd. for 295.0933, Found [M+H]$^{+-}$296.1011.mp: 202–204° C. (decomposed). $^1$H NMR (D$_2$O, NaOD): d.270 (s, 6H, NCH$_2$COOH), 3.04 (s, 6H, PCH$_2$N). $^{13}$C NMR (D$_2$O, NaOD):d 44.55 (d,NCH$_2$COOH, $^3J_{PC}$=5.21 Hz), 53.50 (d, PCH$_2$N, $^1J_{PC}$=9.96 Hz), 179.14 (s, COOH). $^{31}$P NMR (D$_2$O, NaOD): d-38.1(s).

Figure 10:
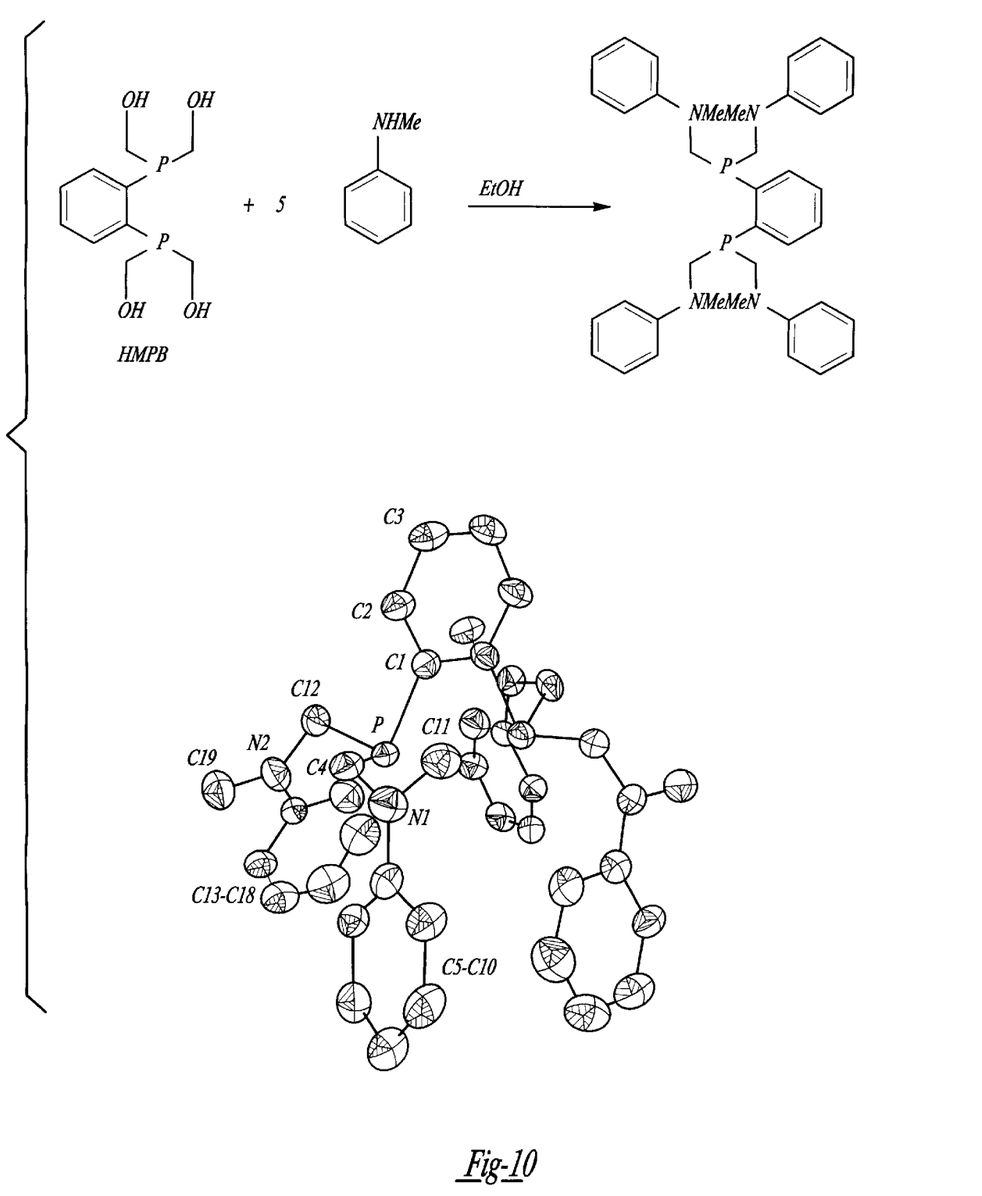
FIG. 10 illustrates the reaction of HMPB with N-methylaniline.

Reaction of N-methylamine with (CH$_2$OH)$_2$PC$_6$H$_4$P(CH$_2$OH)$_2$) (FIG. 10)

N-methylaniline (4.23 mmol) was added dropwise to HMPB (0.850 mol) in ethanol (5 mL) at 25° C. The reaction was stirred under dry nitrogen for one hour. The product was filtered off and dried in vacuo to give the analytically pure compound in 90% yield as a white solid. Crystals suitable for x-ray analysis were obtained from an ethyl acetate solution at −20° C. Anal. Calcd. for $C_{38}H_{44}N_4P_2$.C, 73.76; H, 7.17; N, 9.05. Found: C, 73:60: H, 7.05: N, 9.02. HRFAB Calcd. for $C_{38}H_{44}N_4P_2$618.3041, Found $[M+H]^+$=6.19.3095. mp: 88–90° C. $^1$H NMR (CDCl$_3$): d 2.76 (s, 12H, NCH$_3$), 3.83 (t, 8H, PCH$_2$N), 6.63–6.68 (m, 12H, MeNC$_6$H$_5$-o,p), 7.07–7.19 (m, 8H, MeNC$_6$H$_5$-m), 7.39–7.44 (m, 2H, PC$_6$H$_4$-m), 7.59–7.64 (m, 2H, PC$_6$H$_4$-o), $^{13}$C (CDC$_{13}$) NMR:d 39.2 (t, NCH$_3$, $^3J_{PC}$=3.34 Hz), 53.8 (t, PCH$_2$N, $^1J_{PC}$=4.53 Hz), 113.4 (t, MeNC$_6$H$_5$-o), 116.9 (s, MeNC$_6$H$_5$-p), 128.9 (s, MeNC$_6$H$_5$-m), 129.4 (s, PC$_6$H$_4$-m), 131.3 (t, PC$_6$H$_4$-o, $^3J_{PC}$=3.77), 143.9 (t, PC$_6$H$_4$, $^1J_{PC}$=5.28 Hz), 149.4 (s, MeNC$_6$H$_5$). $^{31}$P (CDCl$_3$ NMR:d-43.6 (s).

Figure 11:
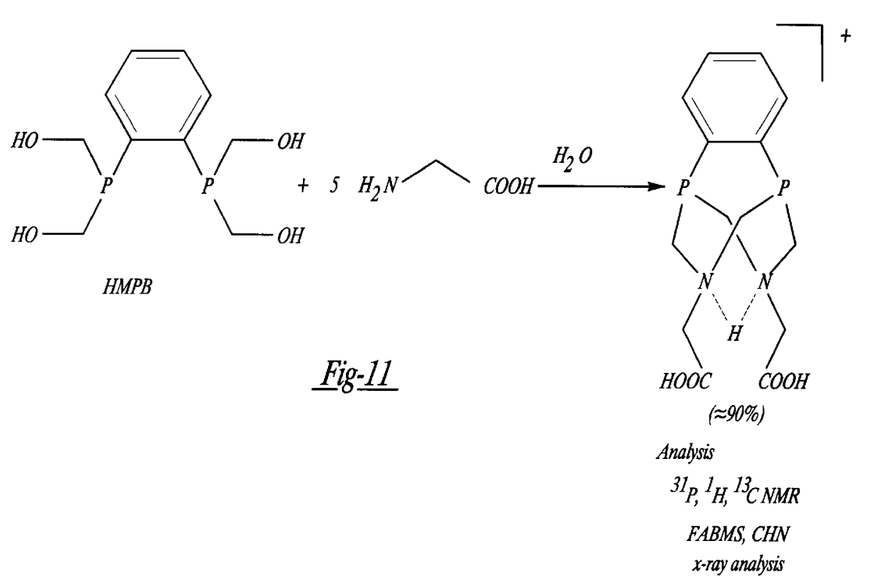
FIG. 11 illustrates an alternative reaction scheme of HMPB with glycine.

Reaction of $(CH_2OH)_2PC_6H_4P(CH_2OH)_2$ with Glycine (FIG. 11)

HMPB (1.910 mmol) in water (5 mL) was added dropwise to glycine (9.603 mmol) also in water (10 mL) at 25° C. The reaction mixture was continuously stirred under dry nitrogen for one hour. The product was filtered off, washed with water and dried in vacuo to give the analytically pure compound in 80% yield. Crystals suitable for x-ray analysis were obtained from MeOH/HCL1 at 0° C. Anal. Calcd. for $C_{14}H_{18}N_2O_4P_2$; C, 49.42; H, 5:33; N, 8:24 Found: C, 46:81; H, 5:48: N, 7:86. HRFAB Calcd. for 340.0742, Found $[M+H]^+$=341.0820.mp: 210–212° C. $^1$H NMR (D$_2$O+NaOD): d2.82 (s, 4H, NCH$_2$COOH), 2.84–2.94 (t, 4H, PCH$_2$N), 3.21–3.27 (dd, 4H, PCH$_2$N), 7.20–7.24 (m, 2H, PC$_6$H$_4$m), 7.53–7.81 (m, 2H, PC$_6$H$_4$-o). $^{13}$C NMR (D$_2$O+NaOD): d 50.2 (d, PCH$_2$N, $^1J_{PC}$=15.09 Hz), 65.2 (s, NCH$_2$COOH), 130.5 (s, PC$_6$H$_4$-m), 137.8 (d, PC$_6$H$_4$-o, $^1J_{PC}$=52.8 Hz), 142.0 (s, (PC$_6$H$_4$), 178.8 (s, COOH) $^{31}$P NMR (D$_2$O+NaOD): d-9-9 (s)

Figure 12:
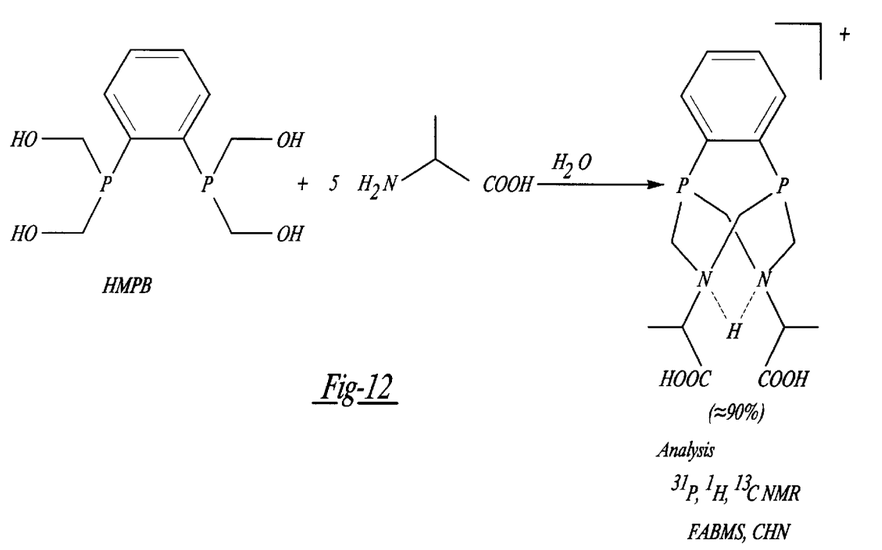
FIG. 12 illustrates the reaction of HMPB with alanine.

Reaction of $(CH_2OH)_2PC_6H_4P(CH_2OH)_2$ with Alanine (FIG. 12)

HMPB (3.282 mmol) in water (15 mL) was added dropwise to alanine (16.82 mmol) also in water (15 mL) at 25° C. The reaction was continuously stirred under dry nitrogen at room temperature for one hour. The product was filtered off, washed with water and dried in vacuo to give the analytically pure product in 80% yield. Anal. Calcd. for $C_{16}H_{22}N_2O_4P_2$: C, 55.20; H, 6.02; N, 7.61. Found: C, 50.02: H, 6.77: N, 7.55. HRFAB Calcd. for 368.1055. Found $[M+H]^+$=369.1133. mp: 208–210° C. $^1$H NMR (D$_2$O+NaOD): d.0.83 (d, 6H, NCHCH$_3$COOH), 2.73–2.82 (m, 4H, NCHCH$_3$COOH, PCH$_2$N), 2.91–3.07 (dd, 2H, PCH$_2$N), 3.14–3.21 (m, 4H, PCH$_2$N), 7.12–7.15 (m, 2H, PC$_6$H$_4$-m), 7.44–7.52 (m, 2H, PC$_6$H$_4$-o). $^{13}$C NMR (D$_2$O+NaOD): d 15.1 (s, NCHCH$_3$COOH), 45.8 (s, PCH$_2$N), 48.8 (d, PCH$_2$N, $^1J_{PC}$=12.8 Hz), 67.4 (s, NCHCH$_3$COOH), 130.3 (d, PC$_6$H$_4$-m $^3J_{PC}$=18.1 Hz), 137.9 (d, PC$_6$H$_4$-o $^2J_{PC}$=51.3 Hz), 142.3 (s, PC$_6$H$_4$), 182.0 (s, NCHCH$_3$COOH). $^{31}$P NMR (D$_2$O+NaOD): d 8.3 (s).

Reaction of $(CH_2OH)_2PC_6H_4P(CH_2OH)_2$ with Diethylamine

Diethylamine (9.71 mmol) was added dropwise to HMPB (9.76 mmol) in ethanol (10 mmL) at 25° C. The reaction was stirred under dry nitrogen for one hour. The solvent and excess diethylamine was removed in vacuo to obtain a viscous oil. The residue was suspended in water (10 mL) and extracted with CH$_2$Cl$_2$ (3×10 mL). The combined organic fractions were concentrated to approximately 10 ml and purified on a silica gel column to give the analytically pure product. $^1$H NMR (CDCl$_3$): d 0.92–1.01 (m, 24H, NCH$_2$CH$_3$), 2.49–2.81 (m, 16H, NCH$_2$CH$_3$), 3.02–3.14 (m, 8H, PCH$_2$N), 7.28–7.34 (m, 2H, PC$_6$H$_4$-m), 7.46–7.53 (m, 2H, PC$_6$H$_4$-o). $^{13}$C(CDCl$_3$NMR:d 12.10 (s, NCH$_2$CH$_3$), 48.18 (s, NCH$_2$CH$_3$), 55.30 (s, PCH$_2$N), 128.56 (s, PC$_6$H$_4$-m), 131.06 (s, PC$_6$H$_4$-o), 144.88 (t, PC$_6$H$_4$ $^1J_{PC}$=7.09 Hz). $^{31}$P (CDCl$_3$) NMR:d-60.3 (s).

Figure 13:
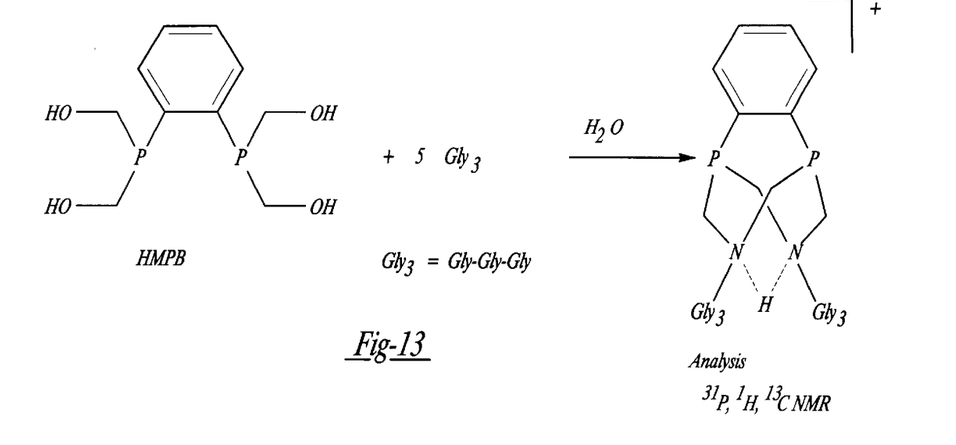
FIG. 13 illustrates the reaction of HMPB with Gly-Gly-Gly.

Reaction of $(CH_2OH)_2PC_6H_4P(CH_2OH)_2$ with Gly-Gly-Gly (FIG. 13)

HMPB (9.50 mmol) in water (5–10 mL) was added dropwise to gly-gly-gly (50.5 mmol) also in water (5–10 mL) at 25° C. After stirring for three hours, the reaction mixture was concentrated and chromatographed by HPLC to give the analytically pure compound. 1 H NMR (D20+NaOD): d 13C (D20+NaOD): d 31 P NMR (D20+NaOD): d-8.6 (s).

Figure 14:
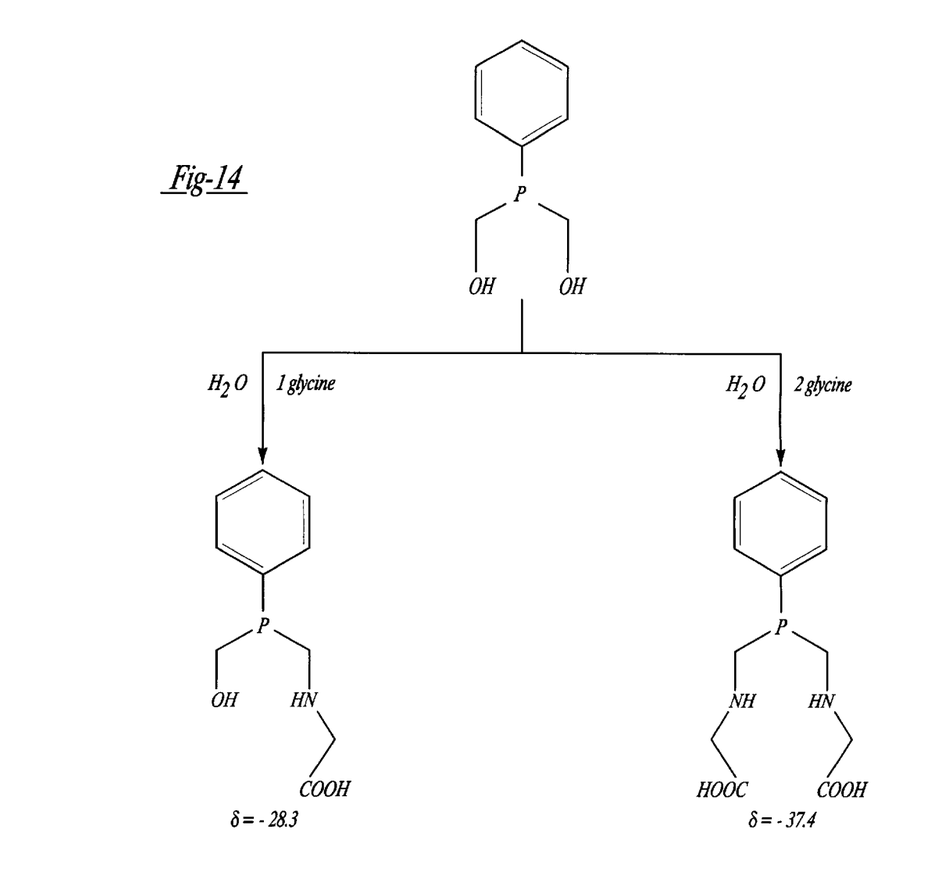
FIG. 14 illustrates the reaction of PhP (CH$_2$OH)$_2$ with glycine.

Reaction of PhP(CH$_2$OH)$_2$ with Glycine (FIG. 14)

This reaction was carried out to investigate the possibility of producing phosphine-amine conjugates that contain an unreacted p—CH$_2$—OH group (Scheme 6). In fact, this reaction did produce the phosphine-amine conjugate with a dangling hydroxy group when PhP (CH$_2$OH)$_2$ was allowed to interact with one equivalent of glycine in water. The yields of this product, as estimated by $^{31}$P NMR analysis, were in the 80–85% range while a small amount (~5%) of the bis product was also formed. The reaction of PhP (CH$_2$OH)$_2$ with two equivalents of glycine produced, as expected, the bis product in >95% yield (FIG. 14). These reaction proceed smoothly in the pH range 2.9.

Figure 15:
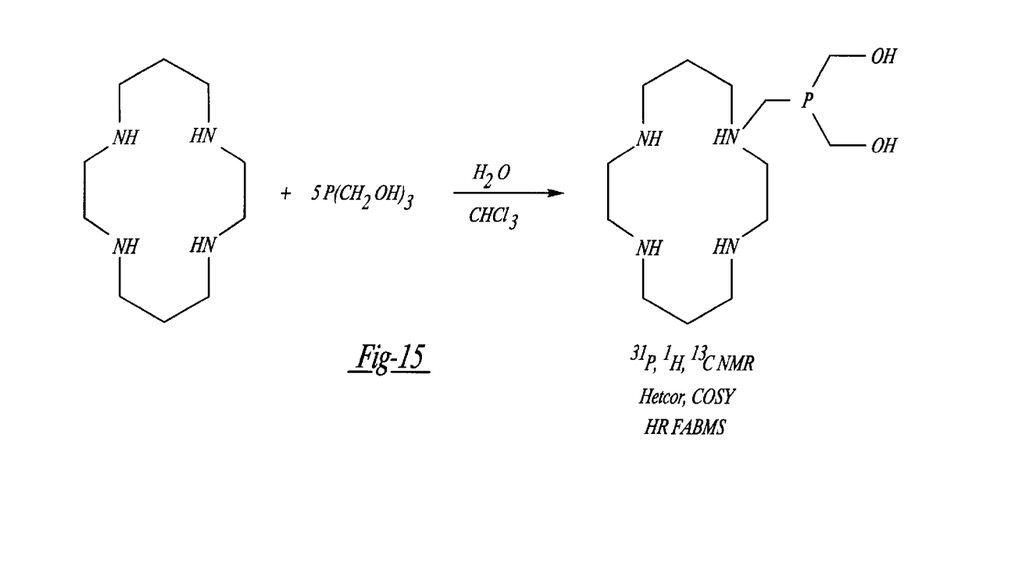
FIG. 15 illustrates the reaction of P(CH$_2$OH)$_3$ with cyclam.

Reaction of P(CH$_2$OH)$_3$ with Cyclam (FIG. 15)

This reaction was carried out to investigate the steric effects of amines on the product distributions in their reaction with P(CH$_2$OH)$_3$. In fact, when cyclam was allowed to interact with P(CH$_2$OH)$_3$, only the mono product that contained one cyclam unit per THP (FIG. 15) was obtained. This demonstrates that the steric bulk can be effectively used to dictate the distribution of products in the reactions of hydroxymethyl phosphines with amines. Experimental details are summarized below.

Cyclam (5×10$^{-3}$ mol.) in chloroform (10 mL) was added to THP (2.5×10$^{-2}$ mol.) in 10 mL of distilled water under dry nitrogen at room temperature for three hours. The aqueous layer was extracted and concentrated under reduced pressure. The product was loaded onto a preconditioned Waters Sep-Pak VAC C18 column (10 g, 35 mL) and eluted with distilled water followed by acetonitrile. The acetonitrile fractions were collected and the solvent was removed under reduced pressure to give the analytically pure product. LRFAB Calcd. for 306.2 Found $[M+Na]^+$m/z=329.2. $^1$H NMR (D$_2$O)δ3.91 (d,2H,CH$_2$OH), 3.58–1.38 (m, 2OH, cyclam hydrogens). $^{31}$P NMR (D20)δ–49.2(s).

Figure 16:
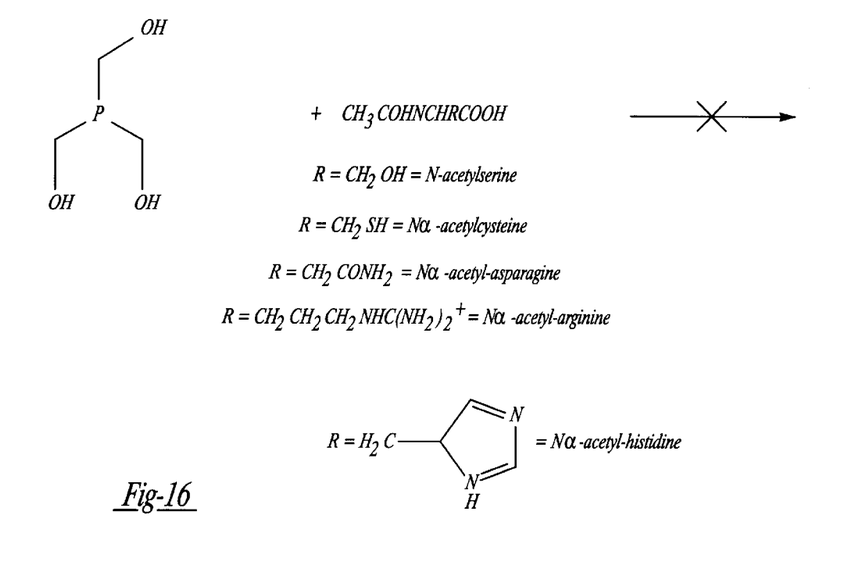
FIG. 16 illustrates that HMP groups do not react with alcohol (Ser), carboxylic acid, primary amide (Asn), secondary amide, guanidine (Arg), and imidazole (His) groups.

Experiments Demonstrating that HMP Groups do not React with Alcohol (Ser), Carboxylic Acid, Primary Amide (Asn), Secondary Amide, Guanidine (Arg) and Imidazole (His) Groups (FIG. 16)

Reaction of THP with N-methylacetamide

An aerated, aqueous solution (10 mL) of THP (4.56×10$^{-3}$ mol) was added dropwise to N-methylacetamide (1×10$^2$ mol). The pH was adjusted with 0.2M KOH (1 mL aliquots) until the pH was greater than 8.0 and the reaction was incubated at room temperature in excess of twenty minutes. The reaction was monitored by $^{31}$P NMR. Only the $^{31}$P resonance of the unreacted phosphine in THP (i.e., −24 ppm) was observed.

Reaction of THP with N-α-acetyl-L-asparagine

An aqueous solution (4 mL) of THP (9.67×10$^{-4}$ mol) was added dropwise to Nα-acetyl-L-asparagine (2.87×10$^{-3}$ mol) in water (10 mL). The pH was adjusted with 0.2 M KOH. The $^{31}$P NMR spectrum was recorded at a pH of 2.25, 5.20, 7.20 and 10.00. Only the resonance of the unreacted phosphine in THP (i.e., −24 ppm) was observed.

11

Reaction of THP with N₂-acetyl-L-arginine

An aqueous solution (5 mL) of the THP ($1.29 \times 10^{-3}$ mol) was added drowse to Nα-acetyl-L-argentine ($3.96 \times 10^{-3}$ mol) in water (20 ml). The pH was adjusted with 0.2 M OH. The $^{31}$P NOR spectrum was recorded at pH of 4.50, 9.15 and 10.18. Only the $^{31}$P resonance of the unreacted phosphine in THP (i.e., −24 ppm) was observed.

Reaction of THP with N-α-acetyl-L-histidine

An aqueous solution (4 mL) of THP ($8.07 \times 10^{-3}$ mol) in water (8 mL). The pH was adjusted with 0.2M KOH. The $^{31}$P NMR spectrum was recorded at a pH of 5.51, 6.10 and 10.05. Only the $^{31}$P resonance of the unreacted phosphine in THP (i.e., −24 ppm) was observed.

Reaction of THP with N-acetyl-DL-serine

An aerated, aqueous solution (4 mL) of THP ($1.05 \times 10^{-3}$ mol) was added dropwise to N-acetyl-DL-serine ($2.92 \times 10^{-3}$ mol) in water (10 mL). The pH was adjusted with 0.2M KOH. The $^{31}$P NMR spectrum was recorded at a pH of 4.50, 8.20 and 10.10. Only $^{31}$P resonance of the unreacted phosphine in THP (i.e., −24 ppm) was observed.

Reaction of $P(CH_2OH)_3$ with L-Cysteine

An aqueous solution of $P(CH_2OH)_3$ was allowed to react with a solution of L-cysteine attached to carboxymethyl group (~20 fold excess). This reaction was carried out at pH 2, 4.5, 7.4 and 9.0. Typically, the mixture was stirred at 25° C. for six to eight hours. Examination of the reaction mixtures (at all the four pH) by $^{31}$P NMR spectroscopy showed the pressure of a signal at −23 ppm indicating that $P(CH_2OH)_3$ did not react with —SH or —COOH groups.

Throughout this application various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

REFERENCES CITED

Angolini, *Tetrahedron*, 46, pp. 1791 (1990).
Annuziato et al., *Bioconjugate Chem.* 54, pp. 212, 218 (1993).
Brewster et al., "The Potential Uses of Cyclodextrins in Parenteral Formulations" *J. Parenteral Sci. Technol.*, 43, pp. 231–240 (1989).
Cox et al., *J. Chem. Soc., Perkin Trans.*, 1, pp. 2567–2576 (1990).
Duchene et al., "Pharmaceutical Applications of Cyclodextrins" in *Cyclodextrins and Their Industrial Uses*, pp. 211–257, Editions de Sante Paris (1987).
Eisch and Sanchez, *J. Org. Chem.*, 51, pp. 1848 (1986).
Frank and Drake, *J. Org. Chem.*, 37, pp. 2752 (1972).
Hayashi and Ikada, *J. Appl. Polym Sci.*, 42, pp. 85 (1991).
Kline et al., *Bioconjugate Chemistry* 2, pp. 26–31 (1991).
Krajwska et al., *J. Chem. Tech. Biotechnol.*, 48, pp. 337 (1990).
Lewis et al., *Bioconjugate Chemistry*, 5, pp. 565–576 (1994).

12

Liu et al., *Bioconjugate Chemistry*, 7, pp. 63–71 (1996).
Moi et al., *J. MA. Chem. Soc.*, 110, pp. 6266–6267 (1988).
Petach et al., *J. Chem. Soc. Chem. Commun.*, pp. 2181 (1994)
Reaves and Guthrie, *Ind. Eng. Chem.*, 48, pp. 64 (1956).
Schubiger et al., *Bioconjugate Chemistry*, 7, pp. 165–179 (1996).

What is claimed is:

1. A method of forming phosphine-amine conjugates, said method comprising the steps of:
   reacting a hydroxymethyl phosphine group of an amine-free first molecule with at least one free amine group of a second molecule to covalently bond the first molecule with the second molecule through an aminomethyl phosphorus linkage said first and second molecule is a peptide or protein.

2. A method as set forth in claim 1, wherein said reacting step takes place over a pH range of approximately 2–9.

3. A method as set forth in claim 1, wherein the structure of the first molecule containing the hydroxymethyl phosphate group is $RP(CH_2OH)_2$ wherein R is selected from the group consisting of —$CH_2OH$, H, $C_2H_5$, $C_6H_5$, —COOH, $COOCH_3$, and $COOC_2H_5$.

4. A method as set forth in claim 1, wherein the at least one free amine group is selected from the group consisting of primary and secondary amines.

5. A method as set forth in claim 1, wherein the second molecule is a drug.

6. A method as set forth in claim 1, wherein the second molecule is a probe.

7. A method as set forth in claim 1, wherein the second molecule is a toxin.

8. A method as set forth in claim 1, wherein the second molecule is a radioactive moiety.

9. A method as set forth in claim 1, wherein the second molecule is a biomolecule.

10. A method as set forth in claim 9, wherein the biomolecule is selected from the group consisting of monoclonal antibodies and steroids.

11. A method as set forth in claim 1, wherein the second molecule containing the amino group is affixed to a solid support.

12. A method as set forth in claim 11, wherein the solid support is a separation column.

13. A method as set forth in claim 11, wherein the solid support is a resin.

14. A method as set forth in claim 11, wherein the solid support is a solid matrix.

15. A method as set forth in claim 1, wherein the molecule having the hydroxymethyl phosphine group is attached to another chemically active group.

16. A method as set forth in claim 15, wherein the chemically active group is the same as the hydroxymethyl phosphine containing molecule.

17. A method as set forth in claim 15, wherein the chemically active group is different than the hydroxymethyl phosphine containing molecule.

18. A method as set forth in claim 1 further comprising the step of preforming a molecule having a free hydroxymethyl side chain attached thereto.

19. A phosphine-amine conjugate made by the method as set forth in claim 1.

20. A phosphine-amine conjugate, said conjugate comprising:
   a first molecule comprising an amine-free hydroxymethyl phosphine group covalently bound to at least one free amine group of a second molecule to form an aminomethyl phosphorus linkage said first and second molecule is a peptide or protein.

21. A conjugate as set forth in claim 20, wherein the structure of said first molecule containing the hydroxymethyl phosphine group is $RP(CH_2OH)_2$, wherein R selected from the group consisting of —$CH_2OH$, H, $C_2H_5$, $C_6H_5$, COOH, $COOCH_3$, and $COOC_2H_5$.

22. A conjugate as set forth in claim 20, wherein said at least one free amine group is selected from the group consisting of primary and secondary amines.

23. A conjugate as set forth in claim 20, wherein said second molecule is a drug.

24. A conjugate as set forth in claim 20, wherein said second molecule is a probe.

25. A conjugate as set forth in claim 20, wherein said second molecule is a toxin.

26. A conjugate as set forth in claim 20, wherein said second molecule is a radioactive moiety.

27. A conjugate as set forth in claim 20, wherein said second molecule is a biomolecule.

28. A conjugate as set forth in claim 27, wherein said biomolecule is selected from the group consisting of monoclonal antibodies and steroids.

29. A conjugate as set forth in claim 20, wherein said second molecule containing said amino group is affixed to a solid support.

30. A conjugate as set forth in claim 29, wherein said solid support is a separation column.

31. A conjugate as set forth in claim 29, wherein said solid support is a resin.

32. A conjugate as set forth in claim 29, wherein said solid support is a solid matrix.

33. A conjugate as set forth in claim 20, wherein said molecule having said hydroxymethyl phosphine group is attached to another chemically active group.

34. A conjugate as set forth in claim 33, wherein said chemically active group is the same as said hydroxymethyl phosphine containing molecule.

35. A conjugate as set forth in claim 33, wherein said chemically active group is different than said hydroxymethyl phosphine containing molecule.

36. A conjugate as set forth in claim 20 further comprising a performing molecule having a free hydroxymethyl side chain attached thereto.

* * * * *